(12) United States Patent
Hofvander et al.

(10) Patent No.: US 11,162,111 B2
(45) Date of Patent: Nov. 2, 2021

(54) PRODUCTION OF INSECT PHEROMONE PRECURSORS IN PLANTS

(71) Applicants: Per Hofvander, Bjärred (SE); Sten Stymne, Landskrona (SE); Christer Löfstedt, Lund (SE); Bao-Jian Ding, Malmö (SE)

(72) Inventors: Per Hofvander, Bjärred (SE); Sten Stymne, Landskrona (SE); Christer Löfstedt, Lund (SE); Bao-Jian Ding, Malmö (SE)

( * ) Notice: Subject to any disclaimer, the term of this patent is extended or adjusted under 35 U.S.C. 154(b) by 381 days.

(21) Appl. No.: 15/764,808

(22) PCT Filed: May 5, 2015

(86) PCT No.: PCT/SE2015/050491
§ 371 (c)(1),
(2) Date: Mar. 29, 2018

(87) PCT Pub. No.: WO2015/171057
PCT Pub. Date: Nov. 12, 2015

(65) Prior Publication Data
US 2018/0282755 A1    Oct. 4, 2018

(30) Foreign Application Priority Data
May 6, 2014   (SE) .................................. 1430065-1

(51) Int. Cl.
*C07C 57/03* (2006.01)
*C07C 69/533* (2006.01)
(Continued)

(52) U.S. Cl.
CPC .......... *C12N 15/8286* (2013.01); *C07C 57/03* (2013.01); *C07C 69/533* (2013.01); *C07C 69/58* (2013.01); *C12N 15/8247* (2013.01)

(58) Field of Classification Search
CPC ........ C07C 57/03; C07C 69/533; C07C 69/58
(Continued)

(56) References Cited

U.S. PATENT DOCUMENTS

2006/0078973 A1    4/2006   Renz et al.

FOREIGN PATENT DOCUMENTS

JP          2007000119 A        1/2007

OTHER PUBLICATIONS

Napier et al.: "Understanding and manipulating plant lipid composition: Metabolic engineering leads the way", Current Opinion in Plant Biology, vol. 19, pp. 68-75.*

(Continued)

*Primary Examiner* — Deborah D Carr
(74) *Attorney, Agent, or Firm* — Benjamin Diederich

(57) ABSTRACT

Wax esters (WE) and triacylglycerols (TAG) can be accumulated in large amounts in plant cells. The present invention relates to insect pheromone precursors which are produced as components of WE or TAG in plants. Further the invention concerns means and methods for the production of plant cells producing WE and/or TAG containing insect pheromone precursors in form of either a fatty acid or a fatty alcohol. Said method uses plants where wax esters are modified by desaturase, fatty acyl reductase and wax ester synthase or the triacylglycerol is modified by a desaturase. Finally the insect pheromone precursors can be extracted and used in the manufacturing of insect pheromones from WE and TAG.

5 Claims, 1 Drawing Sheet

Specification includes a Sequence Listing.

(51) Int. Cl.
    *C07C 69/58*     (2006.01)
    *C12N 15/82*     (2006.01)

(58) Field of Classification Search
    USPC .......................................................... 554/223
    See application file for complete search history.

(56) References Cited

OTHER PUBLICATIONS

Iven et al.: "Wax ester profiling of seed oil by nano-electrospray ionization tandem mass spectrometry", Plant Methods, vol. 9, p. 24.*

Heilmann et al.: "Production of wax esters in plant seed oils by oleosomal cotargeting of biosynthetic enzymes", Journal of Lipid Research, vol. 53, 2012, pp. 2153-2161.*

Ding et al.: "A plant factory for moth pheromone production", Nat. Commun., vol. 5, 2014, p. 3353.*

Nesnerova Pet al.: "First semi-synthetic preparation of sex pheromones", Green Chem, vol. 6, pp. 305-307 (Year: 2004).*

Vanhercke et al: "Metabolic engineering of biomass for high energy density: oilseed-like triacylglycerol yields from plant leaves", Plant Biotechnology Journal, vol. 12, No. 2, pp. 231-239, 2014.*

Ding, B.-J. et al. "A plant factory for moth pheromone production". Nat. Commun. 5:3353 doi: 10.1038/ncomms4353 (2014).; whole document; p. 2, col. 1, line 47-line 50; p. 2, col. 1, line 60—p. 3, col. 1, line 10; p. 6, col. 1, line 24-line 30; p. 7, col. 2, line 3-line 9.

Nesnerova P et al. "First semi-synthetic preparation of sex pheromones", 2004 vol. 6, pp. 305-307, Green Chem; whole document; p. 305, col. 1, line 14-line 26; p. 306, col. 1, line 20-line 23.

Napier Ja et al. "Understanding and manipulating plant lipid composition: Metabolic engineering leads the way", vol. 19, pp. 68-75, Current Opinion in Plant Biology; whole document.

Iven T et al. "Wax ester profiling of seen oil by nano-electrospray ionization tandem mass spectrometry", vol. 9:24, Plant methods; whole document; p. 2, col. 1, line 8-line 16; p. 2, col. 1, line 29-line 44; Abstract.

Heilmann M et al. "Production of wax esters in plant seen oils by oleosomal cotargeting of biosynthetic enzymes", 2012, vol. 53, pp. 2153-2161, Journal of Lipid Research; whole document; p. 2153, col. 2, last four lines.

Bansal et al. "Defining the extreme substrate specificity of Euonymus alatus diacylglycerol acetyltransferase, an unusual membrane-bound O-acyltransferase" Bioscience Report (2016) 36, e00406, doi:10.1042/BSR20160277.

Durrett, et al. "A distinct DGAT with sn-3 acetyltranserase activity that synthesizes unusual, reduced-viscosity oils in Euonymus and transgenic seeds" PNAS; 2010, vol. 107, p. 9464-9469.

Vanhercke, et al. "Metabolic engineering of biomass for high energy density:oilseed-like triacylglycerol yields from plant leaves", vol. 12, pp. 231-239, Plant Biology Journal; pp. 231, 232, 234-236; Figures 1 and 3.

* cited by examiner

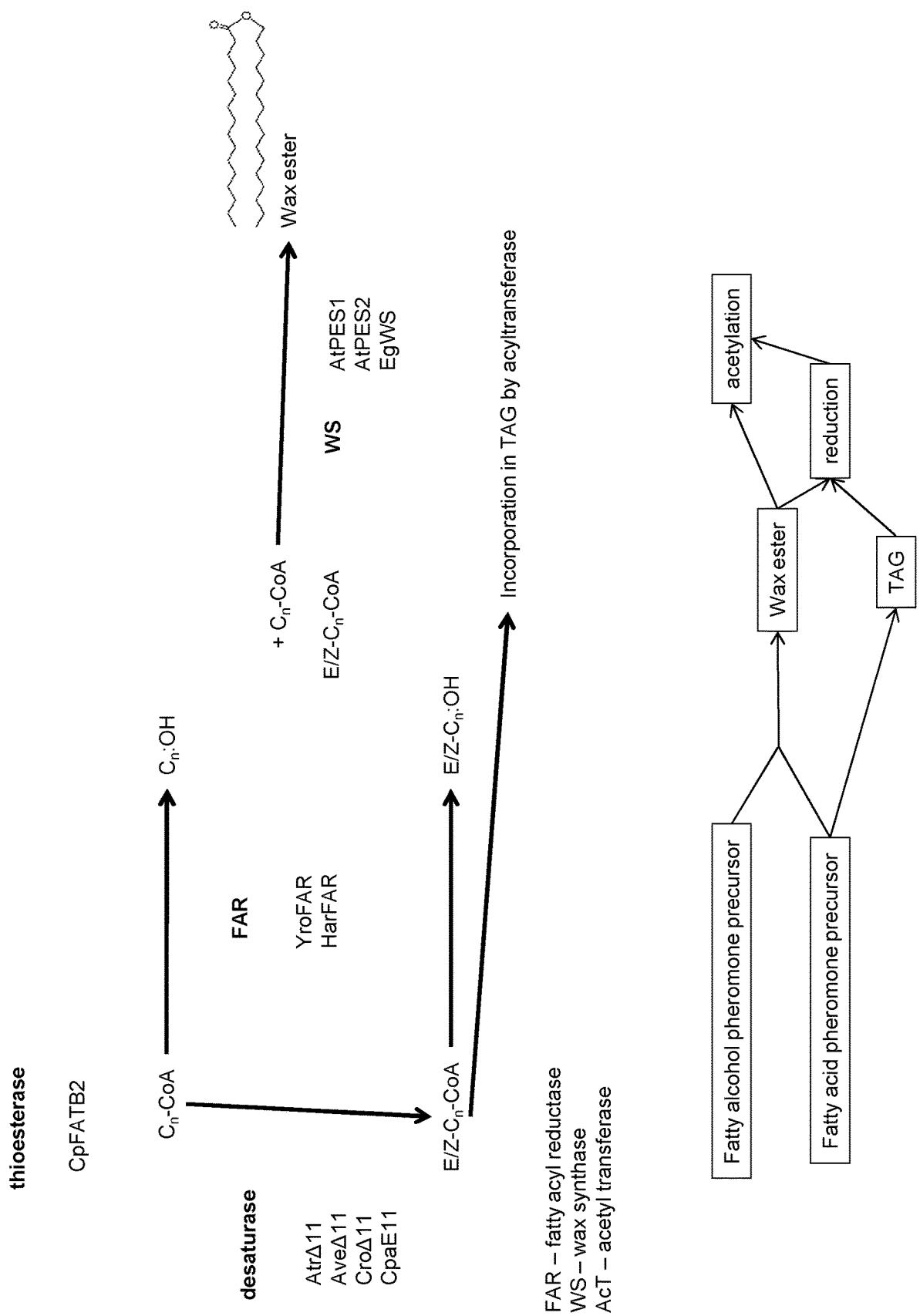

SEQUENCE LISTING

```
<160> NUMBER OF SEQ ID NOS: 15

<210> SEQ ID NO 1
<211> LENGTH: 411
<212> TYPE: PRT
<213> ORGANISM: Cuphea palustris
<220> FEATURE:
<223> OTHER INFORMATION: acyl-ACP thioesterase

<400> SEQUENCE: 1

Met Val Ala Ala Ala Ser Ala Ala Phe Phe Ser Val Ala Thr Pro
1               5                   10                  15

Arg Thr Asn Ile Ser Pro Ser Ser Leu Ser Val Pro Phe Lys Pro Lys
                20                  25                  30

Ser Asn His Asn Gly Gly Phe Gln Val Lys Ala Asn Ala Ser Ala His
            35                  40                  45

Pro Lys Ala Asn Gly Ser Ala Val Ser Leu Lys Ser Gly Ser Leu Glu
        50                  55                  60

Thr Gln Glu Asp Lys Thr Ser Ser Ser Pro Pro Pro Arg Thr Phe
65                  70                  75                  80

Ile Asn Gln Leu Pro Val Trp Ser Met Leu Leu Ser Ala Val Thr Thr
                85                  90                  95

Val Phe Gly Val Ala Glu Lys Gln Trp Pro Met Leu Asp Arg Lys Ser
                100                 105                 110

Lys Arg Pro Asp Met Leu Val Glu Pro Leu Gly Val Asp Arg Ile Val
            115                 120                 125

Tyr Asp Gly Val Ser Phe Arg Gln Ser Phe Ser Ile Arg Ser Tyr Glu
        130                 135                 140

Ile Gly Ala Asp Arg Thr Ala Ser Ile Glu Thr Leu Met Asn Met Phe
145                 150                 155                 160

Gln Glu Thr Ser Leu Asn His Cys Lys Ile Ile Gly Leu Leu Asn Asp
                165                 170                 175

Gly Phe Gly Arg Thr Pro Glu Met Cys Lys Arg Asp Leu Ile Trp Val
                180                 185                 190
```

```
Val Thr Lys Met Gln Ile Glu Val Asn Arg Tyr Pro Thr Trp Gly Asp
            195                 200                 205

Thr Ile Glu Val Asn Thr Trp Val Ser Ala Ser Gly Lys His Gly Met
    210                 215                 220

Gly Arg Asp Trp Leu Ile Ser Asp Cys His Thr Gly Glu Ile Leu Ile
225                 230                 235                 240

Arg Ala Thr Ser Val Trp Ala Met Met Asn Gln Lys Thr Arg Arg Leu
                245                 250                 255

Ser Lys Ile Pro Tyr Glu Val Arg Gln Glu Ile Glu Pro Gln Phe Val
            260                 265                 270

Asp Ser Ala Pro Val Ile Val Asp Asp Arg Lys Phe His Lys Leu Asp
        275                 280                 285

Leu Lys Thr Gly Asp Ser Ile Cys Asn Gly Leu Thr Pro Arg Trp Thr
    290                 295                 300

Asp Leu Asp Val Asn Gln His Val Asn Asn Val Lys Tyr Ile Gly Trp
305                 310                 315                 320

Ile Leu Gln Ser Val Pro Thr Glu Val Phe Glu Thr Gln Glu Leu Cys
                325                 330                 335

Gly Leu Thr Leu Glu Tyr Arg Arg Glu Cys Gly Arg Asp Ser Val Leu
            340                 345                 350

Glu Ser Val Thr Ala Met Asp Pro Ser Lys Glu Gly Asp Arg Ser Leu
        355                 360                 365

Tyr Gln His Leu Leu Arg Leu Glu Asp Gly Ala Asp Ile Val Lys Gly
    370                 375                 380

Arg Thr Glu Trp Arg Pro Lys Asn Ala Gly Ala Lys Gly Ala Ile Leu
385                 390                 395                 400

Thr Gly Lys Thr Ser Asn Gly Asn Ser Ile Ser
                405                 410

<210> SEQ ID NO 2
<211> LENGTH: 329
<212> TYPE: PRT
<213> ORGANISM: Argyrotaenia velutinana
<220> FEATURE:
<223> OTHER INFORMATION: acyl-CoA desaturase

<400> SEQUENCE: 2

Met Ala Pro Asn Ala Glu Asp Ile Glu Thr Asn Met Pro Glu Thr Glu
1               5                   10                  15

Glu Asn Trp Glu Thr Leu Val Ala Pro Gln Ala Ala Pro Arg Lys Tyr
            20                  25                  30

Gln Ile Val Tyr Lys Ser Leu Leu Thr Phe Gly Tyr Gly His Leu Ala
        35                  40                  45

Gly Leu Tyr Gly Leu Tyr Leu Cys Phe Thr Ser Ala Lys Trp Gln Thr
    50                  55                  60

Ile Gly Leu Ala Ile Ile Leu His Ala Met Ala Ile Leu Gly Ile Thr
65                  70                  75                  80

Ala Gly Ala His Arg Leu Trp Thr His Arg Ala Tyr Lys Ala Thr Val
                85                  90                  95

Pro Leu Gln Ile Ile Leu Ile Ile Phe Asn Ser Leu Ser Phe Gln Asn
            100                 105                 110

Ser Ala Phe Thr Trp Ile Arg Asp His Arg Leu His His Lys Tyr Ser
        115                 120                 125

Asp Thr Asp Gly Asp Pro His Asn Ala Thr Arg Gly Phe Phe Tyr Ser
    130                 135                 140
```

```
His Ile Gly Trp Leu Leu Val Arg Lys His Pro Glu Val Met Lys Arg
145                 150                 155                 160

Gly Arg Met Thr Glu Met Ser Asp Ile Tyr Ser Asn Pro Ile Ile Met
                165                 170                 175

Phe Gln Lys Asn Tyr Ala Ile Pro Phe Ile Gly Thr Val Cys Phe Val
            180                 185                 190

Leu Pro Thr Ile Ile Pro Met Tyr Phe Trp Gly Glu Thr Leu Asn Asn
        195                 200                 205

Ala Trp His Ile Thr Val Leu Arg Tyr Ile Phe Ser Leu Asn Cys Ile
210                 215                 220

Phe Leu Val Asn Ser Ala Ala His Leu Tyr Gly Tyr Lys Pro Tyr Asp
225                 230                 235                 240

Lys Asn Ile Leu Pro Ala Glu Asn Lys Ala Ala Ser Ile Ala Ser Phe
                245                 250                 255

Gly Glu Ala Phe His Asn Tyr His His Val Phe Pro Trp Asp Tyr Arg
            260                 265                 270

Ala Ser Glu Leu Gly Asn Ile Thr Met Asn Trp Thr Ile Tyr Phe Ile
        275                 280                 285

Asp Phe Phe Ala Trp Ile Gly Trp Ala Tyr Asp Leu Lys Thr Ala Ser
290                 295                 300

Asp Glu Thr Ile Lys Ser Arg Ile Lys Arg Thr Gly Asp Gly Thr Asp
305                 310                 315                 320

Phe Ser Gly Gln Gln Ile Tyr Ala Arg
                325

<210> SEQ ID NO 3
<211> LENGTH: 335
<212> TYPE: PRT
<213> ORGANISM: Choristoneura rosaceana
<220> FEATURE:
<223> OTHER INFORMATION: acyl-CoA desaturase

<400> SEQUENCE: 3

Met Ala Pro Asn Val Glu Asp Met Glu Ser Asp Leu Pro Glu Ser Glu
1               5                   10                  15

Glu Lys Leu Glu Lys Leu Val Ala Pro Gln Ala Ala Pro Arg Lys Tyr
            20                  25                  30

Gln Ile Ile Tyr Thr Asn Leu Leu Thr Phe Gly Tyr Trp His Ile Ala
        35                  40                  45

Gly Leu Tyr Gly Leu Tyr Leu Cys Phe Thr Ser Ala Lys Trp Gln Thr
    50                  55                  60

Ile Ile Leu Ala Leu Ile Leu Asn Glu Met Ala Ile Leu Gly Ile Thr
65                  70                  75                  80

Ala Gly Ala His Arg Leu Trp Ala His Arg Ser Tyr Lys Ala Thr Val
                85                  90                  95

Pro Leu Gln Ile Ile Leu Ile Ile Phe Asn Ser Leu Ser Phe Gln Asn
            100                 105                 110

Ser Ala Ile His Trp Ile Arg Asp His Arg Met His His Lys Tyr Ser
        115                 120                 125

Asp Thr Asp Gly Asp Pro His Asn Ala Ser Arg Gly Phe Phe Tyr Ser
    130                 135                 140

His Val Gly Trp Leu Leu Val Lys Lys His Pro Glu Val Lys Lys Arg
145                 150                 155                 160

Ala Lys Thr Ile Asp Met Ser Asp Ile Tyr Ser Asn Pro Ile Leu Arg
                165                 170                 175
```

```
Phe Gln Lys Lys Tyr Ala Ile Pro Phe Ile Gly Met Ile Cys Phe Val
            180                 185                 190
Leu Pro Thr Ile Ile Pro Met Tyr Phe Trp Gly Glu Thr Leu Ser Asn
        195                 200                 205
Ala Trp His Ile Thr Met Leu Arg Tyr Val Phe Ser Leu Asn Ser Ile
    210                 215                 220
Phe Leu Val Asn Ser Ala His Leu Tyr Gly Tyr Arg Pro Tyr Asp
225                 230                 235                 240
Lys Asn Ile Leu Pro Ala Glu Asn Lys Met Thr Phe Ile Ala Cys Leu
                245                 250                 255
Gly Glu Asn Phe His Asn Tyr His His Val Phe Pro Trp Asp Tyr Arg
            260                 265                 270
Ala Ser Glu Leu Gly Asn Ile Gly Met Asn Trp Thr Ala Lys Phe Ile
        275                 280                 285
Asp Phe Phe Ala Trp Ile Gly Trp Ala Tyr Asp Leu Lys Thr Ala Ser
    290                 295                 300
Asp Glu Asn Ile Lys Ser Arg Met Lys Arg Thr Gly Asp Gly Thr Asp
305                 310                 315                 320
Val Ser Gly Gln Lys Tyr Ser Cys Glu Ser Ser Glu Val Leu Gln
                325                 330                 335
```

<210> SEQ ID NO 4
<211> LENGTH: 334
<212> TYPE: PRT
<213> ORGANISM: Choristoneura parallela
<220> FEATURE:
<223> OTHER INFORMATION: acyl-CoA desaturase

<400> SEQUENCE: 4

```
Met Ala Pro Asn Val Glu Asp Met Glu Ser Asp Met Pro Glu Ser Glu
1               5                   10                  15
Lys Trp Glu Lys Leu Val Ala Pro Gln Ala Ala Pro Arg Lys Tyr Glu
            20                  25                  30
Ile Ile Tyr Thr Asn Leu Leu Thr Phe Gly Tyr Gly His Ile Ala Gly
        35                  40                  45
Leu Tyr Gly Leu Tyr Leu Cys Phe Thr Ser Ala Lys Trp Gln Thr Val
    50                  55                  60
Ile Leu Ala Ile Ile Leu Asn Glu Met Ala Ile Leu Gly Ile Thr Ala
65                  70                  75                  80
Gly Ala His Arg Leu Trp Ser His Arg Ser Tyr Lys Ala Ala Val Pro
                85                  90                  95
Leu Gln Ile Ile Leu Met Ile Phe Asn Ser Leu Ala Phe Gln Asn Ser
            100                 105                 110
Ala Ile Asn Trp Val Arg Asp His Arg Met His His Lys Tyr Ser Asp
        115                 120                 125
Thr Asp Gly Asp Pro His Asn Ala Ser Arg Gly Phe Phe Tyr Ser His
    130                 135                 140
Val Gly Trp Leu Leu Val Lys Lys His Pro Glu Val Lys Lys Arg Gly
145                 150                 155                 160
Lys Met Ile Asp Met Ser Asp Ile Tyr Ser Asn Pro Val Leu Arg Phe
                165                 170                 175
Gln Lys Lys Tyr Ala Ile Pro Phe Ile Gly Met Ile Cys Phe Val Leu
            180                 185                 190
Pro Thr Ile Ile Pro Met Tyr Phe Trp Gly Glu Thr Leu Ser Asn Ala
        195                 200                 205
```

```
Trp His Ile Thr Met Leu Arg Tyr Val Phe Ser Leu Asn Ser Ile Phe
    210                 215                 220

Leu Val Asn Ser Ala Ala His Leu Tyr Gly Tyr Arg Pro Tyr Asp Lys
225                 230                 235                 240

Asn Ile Leu Pro Ala Glu Asn Lys Ile Ala Leu Ile Ala Cys Leu Gly
                245                 250                 255

Asp Ser Phe His Asn Tyr His Val Phe Pro Trp Asp Tyr Arg Ala
            260                 265                 270

Ser Glu Leu Gly Asn Ile Gly Met Asn Trp Thr Ala Gln Phe Ile Asp
                275                 280                 285

Phe Phe Ala Trp Ile Gly Trp Ala Tyr Asp Leu Lys Thr Ala Ser Asp
290                 295                 300

Glu Asn Ile Asn Ser Arg Met Lys Arg Thr Gly Asp Gly Thr Asp Ile
305                 310                 315                 320

Ser Gly Gln Lys Tyr Ser Cys Glu Ser Ser Glu Val Leu Gln
                325                 330
```

<210> SEQ ID NO 5
<211> LENGTH: 329
<212> TYPE: PRT
<213> ORGANISM: Ostrinia nubilalis
<220> FEATURE:
<223> OTHER INFORMATION: acyl-CoA desaturase

<400> SEQUENCE: 5

```
Met Val Pro Tyr Ala Thr Thr Ala Asp Gly His Pro Glu Lys Asp Glu
1                   5                   10                  15

Cys Phe Glu Asp Asn Glu Ile Lys Ser Asn Ser Leu Pro Lys Leu Glu
                20                  25                  30

Ile Leu Tyr Phe Asn Val Met Thr Phe Thr Phe Leu His Leu Ser Ala
            35                  40                  45

Leu Tyr Gly Leu Tyr Leu Gly Phe Thr Ser Val Lys Trp Ala Thr Ile
        50                  55                  60

Gly Leu Gly Ile Ile Phe Tyr Phe Ala Glu Ile Gly Ile Thr Ala
65                  70                  75                  80

Gly Ala His Arg Leu Trp Ser His Arg Ser Tyr Lys Ala Lys Leu Pro
                85                  90                  95

Leu Glu Ile Leu Leu Met Val Phe Asn Ser Met Ala Phe Gln Asn Thr
            100                 105                 110

Ala Leu Ser Trp Ala Arg Asp His Arg Val His His Lys Cys Pro Asp
        115                 120                 125

Thr Asn Gly Asp Pro His Asn Ala Asn Arg Gly Phe Phe Tyr Ser His
130                 135                 140

Val Gly Trp Leu Met Thr Lys Lys Ser Asp Glu Val Ile Lys Gln Gly
145                 150                 155                 160

Lys Leu Cys Asp Val Ala Asp Leu Tyr Ser Asn Pro Val Leu Arg Phe
                165                 170                 175

Gln Lys Lys Tyr Ala Val Pro Phe Ile Gly Thr Leu Cys Phe Val Leu
            180                 185                 190

Pro Thr Leu Ile Pro Met Tyr Phe Trp Gly Glu Thr Leu Asn Asn Ala
        195                 200                 205

Trp His Phe Asn Met Phe Arg Tyr Val Ile Asn Leu Asn Ala Thr Phe
210                 215                 220

Cys Val Asn Ser Val Val His Lys Trp Gly Tyr Lys Pro Tyr Asp Lys
225                 230                 235                 240
```

```
Asn Ile Cys Pro Thr Gln Asn Val Leu Leu Asn Leu Ala Val Leu Gly
                245                 250                 255

Glu Ala Phe His Asn Tyr His Val Phe Pro Trp Asp Tyr Arg Ala
            260                 265                 270

Ala Glu Leu Gly Asn Gln Lys Met Asn Pro Thr Thr Leu Phe Ile Asp
        275                 280                 285

Phe Phe Ala Trp Ile Gly Trp Ala Tyr Asp Leu Lys Thr Ala Ser Lys
    290                 295                 300

Glu Met Ile Lys Ser Arg Ser Glu Arg Thr Gly Asp Gly Thr Asp Leu
305                 310                 315                 320

Trp Gly His Ser Ala Asp Lys Leu Lys
                325
```

<210> SEQ ID NO 6
<211> LENGTH: 326
<212> TYPE: PRT
<213> ORGANISM: Amyelois transitella
<220> FEATURE:
<223> OTHER INFORMATION: acyl-CoA desaturase

<400> SEQUENCE: 6

```
Met Val Pro Asn Lys Gly Ser Ser Asp Val Leu Ser Glu His Ser Glu
1               5                   10                  15

Pro Gln Phe Thr Lys Leu Ile Ala Pro Gln Ala Gly Pro Arg Lys Tyr
            20                  25                  30

Lys Ile Val Tyr Arg Asn Leu Leu Thr Phe Gly Tyr Trp His Leu Ser
        35                  40                  45

Ala Val Tyr Gly Leu Tyr Leu Cys Phe Thr Cys Ala Lys Trp Ala Thr
    50                  55                  60

Ile Leu Phe Ala Phe Phe Leu Tyr Val Ile Ala Glu Ile Gly Ile Thr
65                  70                  75                  80

Gly Gly Ala His Arg Leu Trp Ala His Arg Thr Tyr Lys Ala Lys Leu
                85                  90                  95

Pro Leu Glu Ile Leu Leu Leu Ile Met Asn Ser Ile Ala Phe Gln Asp
            100                 105                 110

Thr Ala Phe Thr Trp Ala Arg Asp His Arg Leu His His Lys Tyr Ser
        115                 120                 125

Asp Thr Asp Ala Asp Pro His Asn Ala Thr Arg Gly Phe Phe Tyr Ser
130                 135                 140

His Val Gly Trp Leu Leu Val Lys Lys His Pro Glu Val Lys Ala Arg
145                 150                 155                 160

Gly Lys Tyr Leu Ser Leu Asp Asp Leu Lys Asn Asn Pro Leu Leu Lys
                165                 170                 175

Phe Gln Lys Lys Tyr Ala Ile Leu Val Ile Gly Thr Leu Cys Phe Leu
            180                 185                 190

Met Pro Thr Phe Val Pro Val Tyr Phe Trp Gly Glu Gly Ile Ser Thr
        195                 200                 205

Ala Trp Asn Ile Asn Leu Leu Arg Tyr Val Met Asn Leu Asn Met Thr
210                 215                 220

Phe Leu Val Asn Ser Ala Ala His Ile Phe Gly Asn Lys Pro Tyr Asp
225                 230                 235                 240

Lys Ser Ile Ala Ser Val Gln Asn Ile Ser Val Ser Leu Ala Thr Phe
                245                 250                 255

Gly Glu Gly Phe His Asn Tyr His Thr Tyr Pro Trp Asp Tyr Arg
            260                 265                 270
```

```
Ala Ala Glu Leu Gly Asn Asn Arg Leu Asn Met Thr Thr Ala Phe Ile
            275                 280                 285

Asp Phe Phe Ala Trp Ile Gly Trp Ala Tyr Asp Leu Lys Ser Val Pro
        290                 295                 300

Gln Glu Ala Ile Ala Lys Arg Cys Ala Lys Thr Gly Asp Gly Thr Asp
305                 310                 315                 320

Met Trp Gly Arg Lys Arg
                325

<210> SEQ ID NO 7
<211> LENGTH: 455
<212> TYPE: PRT
<213> ORGANISM: Helicoverpa armigera
<220> FEATURE:
<223> OTHER INFORMATION: fatty acyl reductase

<400> SEQUENCE: 7

Met Val Val Leu Thr Ser Lys Glu Thr Lys Pro Ser Val Ala Glu Phe
1               5                   10                  15

Tyr Ala Gly Lys Ser Val Phe Ile Thr Gly Gly Thr Gly Phe Leu Gly
            20                  25                  30

Lys Val Phe Ile Glu Lys Leu Leu Tyr Ser Cys Pro Asp Ile Glu Asn
        35                  40                  45

Ile Tyr Met Leu Ile Arg Glu Lys Lys Gly Leu Ser Val Ser Glu Arg
    50                  55                  60

Ile Lys Gln Phe Leu Asp Asp Pro Leu Phe Thr Arg Leu Lys Asp Lys
65                  70                  75                  80

Arg Pro Ala Asp Leu Glu Lys Ile Val Leu Ile Pro Gly Asp Ile Thr
                85                  90                  95

Ala Pro Asp Leu Gly Ile Asn Ser Glu Asn Glu Lys Met Leu Ile Glu
            100                 105                 110

Lys Val Ser Val Ile Ile His Ser Ala Ala Thr Val Lys Phe Asn Glu
        115                 120                 125

Pro Leu Pro Thr Ala Trp Lys Ile Asn Val Glu Gly Thr Arg Met Met
    130                 135                 140

Leu Ala Leu Ser Arg Arg Met Lys Arg Ile Glu Val Phe Ile His Ile
145                 150                 155                 160

Ser Thr Ala Tyr Thr Asn Thr Asn Arg Glu Val Val Asp Glu Ile Leu
                165                 170                 175

Tyr Pro Ala Pro Ala Asp Ile Asp Gln Val His Gln Tyr Val Lys Asp
            180                 185                 190

Gly Ile Ser Glu Glu Asp Thr Glu Lys Ile Leu Asn Gly Arg Pro Asn
        195                 200                 205

Thr Tyr Thr Phe Thr Lys Ala Leu Thr Glu His Leu Val Ala Glu Asn
    210                 215                 220

Gln Ala Tyr Val Pro Thr Ile Ile Val Arg Pro Ser Val Val Ala Ala
225                 230                 235                 240

Ile Lys Asp Glu Pro Leu Lys Gly Trp Leu Gly Asn Trp Phe Gly Ala
                245                 250                 255

Thr Gly Leu Thr Val Phe Thr Ala Lys Gly Leu Asn Arg Val Ile Tyr
            260                 265                 270

Gly His Ser Ser Tyr Ile Val Asp Leu Ile Pro Val Asp Tyr Val Ala
        275                 280                 285

Asn Leu Val Ile Ala Ala Gly Ala Lys Ser Ser Lys Ser Thr Glu Leu
    290                 295                 300
```

-continued

```
Lys Val Tyr Asn Cys Cys Ser Ser Cys Asn Pro Val Thr Ile Gly
305                 310                 315                 320

Thr Leu Met Ser Met Phe Ala Asp Asp Ala Ile Lys Gln Lys Ser Tyr
            325                 330                 335

Ala Met Pro Leu Pro Gly Trp Tyr Ile Phe Thr Lys Tyr Lys Trp Leu
                340                 345                 350

Val Leu Leu Leu Thr Phe Leu Phe Gln Val Ile Pro Ala Tyr Val Thr
                355                 360                 365

Asp Leu Ser Arg His Leu Ile Gly Lys Ser Pro Arg Tyr Ile Lys Leu
            370                 375                 380

Gln Ser Leu Val Asn Gln Thr Arg Ser Ser Ile Asp Phe Phe Thr Asn
385                 390                 395                 400

His Ser Trp Val Met Lys Ala Asp Arg Val Arg Glu Leu Tyr Ala Ser
                405                 410                 415

Leu Ser Pro Ala Asp Lys Tyr Leu Phe Pro Cys Asp Pro Thr Asp Ile
                420                 425                 430

Asn Trp Thr His Tyr Ile Gln Asp Tyr Cys Trp Gly Val Arg His Phe
            435                 440                 445

Leu Glu Lys Lys Ser Tyr Glu
    450                 455

<210> SEQ ID NO 8
<211> LENGTH: 462
<212> TYPE: PRT
<213> ORGANISM: Ostrinia nubilalis
<220> FEATURE:
<223> OTHER INFORMATION: fatty acyl reductase

<400> SEQUENCE: 8

Met Ser Ala Asn Thr Met Glu Thr Asp Glu Gln Phe Thr Tyr Asn Ser
1               5                   10                  15

Pro Ile Val Asn Phe Tyr Ser Gly Lys Ser Val Phe Val Thr Gly Ala
                20                  25                  30

Thr Gly Phe Leu Gly Thr Val Leu Val Glu Lys Leu Leu Phe Ser Cys
            35                  40                  45

Lys Gly Ile Asn Asn Ile Tyr Ile Leu Ile Lys Gln Thr Glu Asp Leu
50                  55                  60

Thr Ile Glu Ala Arg Ile Leu Asn Tyr Leu Asn Ser Lys Ala Phe His
65                  70                  75                  80

Arg Val Lys Asn Thr Asn Pro Glu Leu Met Lys Lys Ile Ile Pro Ile
                85                  90                  95

Cys Gly Asn Leu Glu Asp Lys Asn Leu Gly Ile Ser Asp Ser Asp Met
            100                 105                 110

Lys Thr Leu Leu Glu Glu Val Ser Ile Val Phe His Val Ala Ala Lys
        115                 120                 125

Leu Leu Phe Lys Met Ser Leu Thr Ala Ala Val Asn Ile Asn Thr Lys
    130                 135                 140

Pro Thr Glu Gln Leu Ile Ala Ile Cys Lys Lys Met Arg Arg Asn Pro
145                 150                 155                 160

Ile Phe Ile Tyr Val Ser Ser Ala Tyr Ser Asn Val Asn Glu Gln Ile
                165                 170                 175

Ile Asp Glu Lys Val Tyr Asn Thr Gly Val Pro Leu Glu Thr Ile Tyr
            180                 185                 190

Asp Thr Leu Asp Thr Glu Asn Thr Arg Ile Thr Asp Ile Phe Leu Asp
        195                 200                 205
```

-continued

Lys Arg Pro Asn Thr Tyr Thr Tyr Ser Lys Ala Leu Ala Glu Val Val
    210                 215                 220

Val Glu Lys Glu Phe Asp Glu Ser Ala Ala Ile Val Arg Pro Ser Ile
225                 230                 235                 240

Ile Val Ser Ser Ile Arg Glu Pro Ile Pro Gly Trp Leu Ser Gly Ser
                245                 250                 255

His Gly Phe Pro Arg Val Val Gly Ala Ala Cys Lys Gly Leu Leu Leu
            260                 265                 270

Arg Trp His Gly Asp Gly Thr Val Cys Asp Leu Ile Pro Val Asp
        275                 280                 285

His Val Ala Asn Leu Ile Ile Ala Ala Ala Trp Glu Ser Asn Glu Arg
    290                 295                 300

Arg Leu Met Gly Asn Lys Gly Val Lys Val Tyr Asn Cys Cys Ser Ser
305                 310                 315                 320

Leu Arg Asn Pro Ile Asp Val Ile Thr Val Lys Thr Cys Ile Lys
                325                 330                 335

Tyr Arg Lys Tyr Phe Gly Thr Arg Thr Met Ser Ile Phe Thr Pro Arg
            340                 345                 350

Phe Ile Met Lys Lys Asn Tyr Phe Ile Tyr Lys Leu Leu Tyr Phe Thr
        355                 360                 365

Tyr His Thr Ile Pro Ala Ala Ile Ile Asp Gly Phe Phe Trp Leu Thr
    370                 375                 380

Gly Arg Thr Pro Ile Met Leu Lys Thr Leu Asp Lys Leu Gly Lys Ile
385                 390                 395                 400

Ser Ser Val Leu Glu Tyr Phe Thr His His Gln Phe Ile Phe Leu Asp
                405                 410                 415

Ser Asn Val Arg Gly Leu Leu Arg Arg Met Glu Gly Thr Asp Arg Gln
            420                 425                 430

Thr Phe Asn Phe Asp Val Thr Glu Ile Glu Trp Glu Pro Tyr Leu Gln
        435                 440                 445

Asn Phe Val Arg Gly Ile Ala Asn Asn Tyr Asp Tyr Ser Met
    450                 455                 460

<210> SEQ ID NO 9
<211> LENGTH: 459
<212> TYPE: PRT
<213> ORGANISM: Ostrinia nubilalis
<220> FEATURE:
<223> OTHER INFORMATION: fatty acyl reductase

<400> SEQUENCE: 9

Met Ser Ala Asn Thr Met Glu Thr Asp Glu Gln Phe Thr Tyr Asn Ser
1               5                   10                  15

Pro Ile Val Asn Phe Tyr Ser Gly Lys Ser Val Phe Val Thr Gly Ala
            20                  25                  30

Thr Gly Phe Leu Gly Thr Val Leu Val Glu Lys Leu Leu Phe Ser Cys
        35                  40                  45

Lys Gly Ile Asn Asn Ile Tyr Ile Leu Ile Lys Gln Thr Glu Asp Leu
    50                  55                  60

Thr Ile Glu Ala Arg Ile Leu Asn Tyr Leu Asn Ser Lys Ala Phe His
65                  70                  75                  80

Arg Val Lys Asn Thr Asn Pro Glu Leu Met Lys Lys Ile Ile Pro Ile
                85                  90                  95

Cys Gly Asn Leu Glu Asp Lys Asn Leu Gly Ile Ser Asp Ser Asp Met
            100                 105                 110

```
Lys Thr Leu Leu Glu Glu Val Ser Ile Val Phe His Leu Ala Ala Lys
            115                 120                 125

Leu Leu Phe Lys Met Ser Leu Ala Ala Ala Val Asn Ile Asn Thr Lys
        130                 135                 140

Ser Thr Glu Gln Leu Ile Ala Ile Cys Lys Lys Met Arg Arg Asn Pro
145                 150                 155                 160

Ile Phe Ile Tyr Val Ser Ser Ala Tyr Ser Asn Val Asn Lys Gln Ile
                165                 170                 175

Ile Asp Glu Lys Val Tyr Ser Thr Gly Val Pro Leu Glu Thr Ile Tyr
            180                 185                 190

Asp Thr Leu Asp Ala Lys Asn Thr Arg Leu Met Asp Ile Phe Leu Asp
        195                 200                 205

Lys Arg Pro Asn Thr Tyr Thr Tyr Ser Lys Ala Leu Ala Glu Val Leu
210                 215                 220

Val Glu Asn Glu Phe Asp Glu Ser Ala Ala Ile Val Arg Pro Ser Ile
225                 230                 235                 240

Ile Ala Ser Ser Ile Arg Glu Pro Ile Pro Gly Trp Leu Ser Gly Ser
                245                 250                 255

His Gly Phe Pro Arg Val Val Glu Ala Ala Cys Lys Gly Leu Leu Leu
            260                 265                 270

Arg Trp His Gly Asp Gly Thr Val Ala Phe Gly Ile Ile Pro Val Asp
        275                 280                 285

His Val Ala Asn Leu Ile Ile Ala Ala Ala Trp Glu Ser Asn Glu Arg
        290                 295                 300

Arg Leu Ile Gly Asn Lys Gly Val Lys Val Tyr Asn Cys Cys Ser Gly
305                 310                 315                 320

Leu Arg Asn Pro Ile Asp Val Ser Thr Val Met Asn Thr Cys Leu Lys
                325                 330                 335

Tyr Arg Lys Tyr Phe Gly Thr Arg Thr Met Ser Ile Ile Thr Pro Arg
            340                 345                 350

Phe Ile Met Lys Lys Asn Tyr Phe Leu Tyr Lys Leu Leu Tyr Phe Thr
        355                 360                 365

Tyr His Thr Ile Pro Ala Ala Ile Ile Asp Gly Phe Phe Trp Leu Thr
370                 375                 380

Gly Arg Thr Pro Met Met Leu Asn Thr Leu His Lys Leu Arg Lys Leu
385                 390                 395                 400

Ser Ser Val Leu Glu Tyr Phe Thr Leu Arg Gln Phe Leu Phe Leu Asp
                405                 410                 415

Ser Asn Val Arg Gly Leu Leu Arg Arg Met Glu Gly Thr Asp Arg Gln
            420                 425                 430

Thr Phe Asn Phe Asp Val Thr Glu Ile Glu Trp Glu Pro Phe Leu Gln
        435                 440                 445

Asn Cys Val Arg Gly Ile Ala Asn Asn Tyr Asp
450                 455

<210> SEQ ID NO 10
<211> LENGTH: 449
<212> TYPE: PRT
<213> ORGANISM: Yponomeuta rorrellus
<220> FEATURE:
<223> OTHER INFORMATION: fatty acyl reductase

<400> SEQUENCE: 10

Met Val Gln Leu Lys Glu Asp Ser Val Ala Ala Phe Tyr Ala Glu Lys
1               5                   10                  15
```

-continued

```
Ser Ile Phe Ile Thr Gly Gly Thr Gly Phe Leu Gly Lys Val Leu Ile
                20                  25                  30
Glu Lys Leu Leu Tyr Ser Cys Lys Ala Val Asp Gln Ile Tyr Val Leu
            35                  40                  45
Ile Arg Lys Lys Lys Asp Gln Thr Pro Ser Glu Arg Ile Ala Gln Leu
        50                  55                  60
Leu Glu Ser Glu Leu Phe Ser Arg Leu Arg Lys Asp Pro Ser Ala
65                  70                  75                  80
Leu Lys Lys Val Val Pro Val Val Gly Asp Leu Thr Met Pro Asn Leu
                85                  90                  95
Gly Leu Ser Ala Ala Val Glu Asp Leu Ile Val Ser Lys Val Thr Val
            100                 105                 110
Ile Phe His Val Ala Ala Thr Val Lys Phe Asn Glu Arg Met Lys Asn
        115                 120                 125
Ala Leu Val Asn Asn Val Glu Ala Thr Arg Glu Val Ile Asn Leu Cys
        130                 135                 140
His Arg Leu Glu Lys Val Asp Ala Phe Ile His Val Ser Thr Ala Tyr
145                 150                 155                 160
Ser Asn Thr Asp Gln Lys Val Val Glu Arg Val Tyr Pro Pro Pro
                165                 170                 175
Ala Pro Leu Ser Glu Val Tyr Ala Phe Val Lys Asn Tyr Gly Asp Asp
            180                 185                 190
Met Asp Ile Ile Gln Asn Leu Leu Asn Gly Arg Pro Asn Thr Tyr Thr
        195                 200                 205
Tyr Thr Lys Ala Leu Ala Glu Asp Ile Val Leu Lys Glu His Gly Gly
210                 215                 220
Ile Pro Thr Ala Ile Ile Arg Pro Ser Ile Val Leu Ser Val Leu Lys
225                 230                 235                 240
Glu Pro Ile Pro Gly Trp Leu Asp Asn Trp Asn Gly Pro Thr Gly Leu
                245                 250                 255
Leu His Ala Ser Ser Gln Gly Val His Cys Ser Met Leu Gly Ser Gly
            260                 265                 270
Ser Asn Val Ala Asp Leu Ile Pro Val Asp Ile Val Thr Asn Leu Met
        275                 280                 285
Ile Val Val Ala Ser Arg Cys Arg Lys Ser Asn Gly Leu Lys Val Tyr
        290                 295                 300
Asn Ser Cys Ser Gly Thr Thr Asn Pro Ile Thr Tyr Gln Ala Phe Thr
305                 310                 315                 320
Lys Met Phe Leu Asp Ser Cys Ile Ser Arg Gly Trp Asn Lys Val Pro
                325                 330                 335
Phe Pro Leu Leu Ile Phe Val Lys Trp Ala Phe Leu Asn Arg Val Leu
            340                 345                 350
Lys Phe Leu Leu Val Ile Val Pro Phe Phe Leu Ile Asp Val Tyr Leu
        355                 360                 365
Arg Phe Phe Gly Lys Pro Asn Tyr Met Arg Met Ile Thr Tyr Thr Lys
        370                 375                 380
Lys Ala Glu Asp Leu Met Thr Phe Phe Thr Ser His Glu Trp Gln Phe
385                 390                 395                 400
Lys Asp Gly Asn Val Arg Asp Leu Ile Asn Met Met Ser Pro Glu Asp
                405                 410                 415
Arg Lys Ile Phe Tyr Cys Asp Pro Glu Glu Ile Gln Trp Lys Pro Tyr
            420                 425                 430
Phe Asp Asp Tyr Cys Val Gly Val Phe Lys Tyr Leu Leu Lys Arg Lys
```

-continued

```
            435                 440                 445

Val

<210> SEQ ID NO 11
<211> LENGTH: 368
<212> TYPE: PRT
<213> ORGANISM: Euglena gracilis
<220> FEATURE:
<223> OTHER INFORMATION: wax synthase

<400> SEQUENCE: 11

Met Asp Phe Leu Gly Phe Pro Asp Ser Glu Ser Glu Arg His Ala His
1               5                   10                  15

Phe Tyr Val Leu Ala Ser Ser Phe Ala Ala Ile Tyr Met Phe Thr
            20                  25                  30

Ile Pro Arg Arg Val Lys Ala Gly Arg Lys Arg Phe Leu Leu Cys Ser
            35                  40                  45

Pro Val Leu Leu Leu Asn Ile Met Gln Pro Tyr Ile Phe Phe Trp Thr
        50                  55                  60

Val Gly Arg His Tyr Cys Asn Phe Ile Pro Leu Tyr Ala Ala Phe Cys
65                  70                  75                  80

Thr Trp Trp Thr Ala Phe Lys Val Met Ala Phe Gly Ile Gly Arg Gly
                85                  90                  95

Pro Leu Cys Gln Phe Ser Ala Phe His Lys Phe Ala Val Val Met Leu
            100                 105                 110

Leu Pro Ile Leu Pro His Gly Asp Thr Asn His Gly Val Lys Asp Glu
        115                 120                 125

Arg Ser Gly Ser Ser Trp Ser Ser Pro Thr Tyr Leu Glu Met Phe Ala
    130                 135                 140

Lys Phe Cys Gly Leu Gly Leu Cys Thr Tyr Gly Ile Ser Gln Leu Ser
145                 150                 155                 160

His Asp Gly Phe Pro Val Leu Tyr Asn Val Phe Leu Ser Leu Ile Met
                165                 170                 175

Tyr Leu His Ile Cys Val Gln Tyr Thr Gly Ser Asn Leu Ala Thr Ser
            180                 185                 190

Lys Val Leu Gln Val Pro Leu Ser Asp Gly Met Asn Gln Pro Tyr Phe
        195                 200                 205

Ser Thr Ser Leu Ser Asn Phe Trp Gly Arg Arg Trp Asn Leu Val Ala
    210                 215                 220

Ser Ser Ser Leu Arg His Val Val Tyr Asp Pro Ile Arg Glu Gly Arg
225                 230                 235                 240

Leu Val Pro Lys Gly His Pro Glu Glu Lys Pro Gly Gly Lys Glu
                245                 250                 255

Val Ser Arg Lys Val Leu Gly Ser Leu Met Ala Phe Leu Val Ser Gly
            260                 265                 270

Ile Met His Glu Tyr Ile Leu Trp Leu Ala Thr Gly Phe Trp Ser Gly
        275                 280                 285

Gln Met Leu Leu Phe Phe Val Val His Gly Val Ala Val Ala Ala Glu
    290                 295                 300

Arg Val Ala Lys Val Ala Trp Ala Arg His Gly Leu Pro Ala Ile Pro
305                 310                 315                 320

Cys Ala Val Ser Ile Pro Met Thr Ile Gly Phe Leu Phe Gly Thr Ala
                325                 330                 335

Glu Leu Leu Phe Tyr Pro Pro Ile Phe Ser Ala Asn Trp Ala Glu His
            340                 345                 350
```

```
Gly Val Ala Asp Leu Arg Arg Gln Phe Arg Ser Leu Gly Leu Ser Val
            355                 360                 365

<210> SEQ ID NO 12
<211> LENGTH: 290
<212> TYPE: PRT
<213> ORGANISM: Gallus gallus
<220> FEATURE:
<223> OTHER INFORMATION: wax synthase

<400> SEQUENCE: 12

Met Lys Ile Glu Phe Ala Pro Leu Ser Leu Pro Leu Gln Arg Arg Leu
1               5                   10                  15

Gln Thr Ala Ala Val Val Gln Trp Val Phe Ser Phe Leu Cys Leu Ala
            20                  25                  30

Gln Cys Cys Thr Ala Ala Phe Ile Gly Leu Leu Phe Thr Arg Phe Trp
        35                  40                  45

Leu Leu Ser Val Leu Tyr Ala Ala Trp Trp Phe Val Asp Arg Glu Ala
    50                  55                  60

Pro Leu Arg Gly Gly Arg Arg Ile His Met Val Arg Asn Ser Ala Val
65                  70                  75                  80

Trp Arg His Met Arg Asp Phe Phe Pro Val Thr Leu Val Lys Thr Ala
                85                  90                  95

Glu Leu Asp Pro Arg Gln Asn Tyr Leu Val Gly Phe His Pro His Gly
            100                 105                 110

Val Leu Ala Val Gly Ala Phe Ile Asn Phe Gly Thr Glu Ala Thr Gly
        115                 120                 125

Phe Ser Thr Ile Phe Pro Gly Ile Thr Pro His Leu Met Met Leu Ser
    130                 135                 140

Leu Trp Phe Arg Val Pro Phe Leu Arg Asp Tyr Leu Met Ser Gly Gly
145                 150                 155                 160

Leu Val Ser Ser Asp Lys Glu Ser Ala Tyr His Val Leu Gln Arg Pro
                165                 170                 175

Glu Gly Gly Asn Leu Leu Ala Ile Ile Val Gly Gly Ala Gln Glu Ala
            180                 185                 190

Leu Asp Ala Arg Pro Gly Ser Cys Thr Leu Leu Lys Asn Arg Lys
        195                 200                 205

Gly Phe Val Arg Val Ala Ile Glu Gln Gly Thr Pro Leu Val Pro Ala
    210                 215                 220

Phe Ser Phe Gly Glu Asn Glu Leu Phe Asp Gln Val Ser Asn Pro Lys
225                 230                 235                 240

Gly Ser Trp Leu Arg Trp Ile Gln His Arg Leu Gln Gln Ile Met Gly
                245                 250                 255

Ile Ser Leu Pro Leu Phe His Ala Arg Gly Ile Phe Gln Tyr Ser Phe
            260                 265                 270

Gly Leu Val Pro Tyr Arg Arg Pro Ile Asn Thr Leu Gly Ser Gln Phe
        275                 280                 285

Pro Cys
    290

<210> SEQ ID NO 13
<211> LENGTH: 362
<212> TYPE: PRT
<213> ORGANISM: Gallus gallus
<220> FEATURE:
<223> OTHER INFORMATION: wax synthase
```

<400> SEQUENCE: 13

```
Met Lys Thr Ile Ile Ala Ala Cys Ser Gln Asn Leu Ser Gly Ser Arg
1               5                   10                  15

Ala Ser Leu His Ala Ala Leu Arg Thr Leu Leu Ala Val Pro Trp Pro
            20                  25                  30

Ser Gln Arg Asp Val Arg Ala Trp Leu Gln Leu Leu Ala Val Leu Gln
        35                  40                  45

Trp Val Leu Ser Phe Leu Leu Leu Gly Pro Val Thr Leu Val Leu Leu
    50                  55                  60

Ile Tyr Leu Val Phe Thr Arg Phe Trp Pro Ile Ser Ala Leu Tyr Leu
65                  70                  75                  80

Ala Trp Val Ile Phe Asp Trp Asp Thr Pro Glu Lys Gly Arg Arg
                85                  90                  95

Leu Pro Cys Leu Arg Arg Trp Ser Val Trp Arg His Phe Arg Asp Tyr
            100                 105                 110

Phe Pro Val Lys Leu Val Lys Thr His Asp Leu Ser Pro Gly His Asn
        115                 120                 125

Tyr Ile Ile Gly Ser His Pro His Gly Ile Leu Cys Val Gly Ala Phe
    130                 135                 140

Cys Asn Phe Ile Thr Gly Ser Thr Gly Phe Ser Glu Leu Phe Pro Gly
145                 150                 155                 160

Ile Arg Pro Phe Leu Thr Thr Leu Ala Gly Asn Phe Arg Leu Pro Leu
                165                 170                 175

Phe Arg Glu Tyr Leu Met Ser Gly Gly Leu Cys Pro Val Thr Arg Arg
            180                 185                 190

Ala Ile Gly His Leu Leu Ser Lys Asn Gly Thr Gly Asn Ala Val Ala
        195                 200                 205

Ile Val Ile Gly Gly Ala Ala Glu Ser Leu Ser Cys Ser Pro Gly Val
    210                 215                 220

Thr Thr Leu Ile Leu Lys Asn Arg Lys Gly Phe Val Arg Met Ala Leu
225                 230                 235                 240

Gln His Gly Ala Phe Leu Val Pro Ser Phe Ser Phe Gly Glu Asn Glu
                245                 250                 255

Leu Phe Arg Gln Val Val Phe Glu Glu Gly Ser Trp Met Arg Ala Val
            260                 265                 270

Gln Gln Arg Phe Gln Lys Met Met Gly Phe Ala Pro Cys Val Phe Tyr
        275                 280                 285

Gly Arg Gly Leu Thr Ser Val Arg Ser Arg Gly Phe Leu Pro Tyr Ala
    290                 295                 300

Arg Pro Ile Thr Thr Val Val Gly Glu Pro Val Thr Val Pro Lys Ile
305                 310                 315                 320

Glu Glu Pro Ser Ser Glu Val Val Asp Leu Tyr His Gly Met Tyr Val
                325                 330                 335

Arg Ser Leu Leu Lys Leu Phe Asn Asp Asn Lys Thr Lys Ala Ser Ser
            340                 345                 350

Trp Arg Gln Lys Ser Thr Trp Pro Arg Ser
        355                 360
```

<210> SEQ ID NO 14
<211> LENGTH: 352
<212> TYPE: PRT
<213> ORGANISM: Simmondsia chinensis
<220> FEATURE:
<223> OTHER INFORMATION: wax synthase

<400> SEQUENCE: 14

```
Met Glu Val Glu Lys Glu Leu Lys Thr Phe Ser Glu Val Trp Ile Ser
1               5                   10                  15

Ala Ile Ala Ala Ala Cys Tyr Cys Arg Phe Val Pro Ala Val Ala Pro
            20                  25                  30

His Gly Gly Ala Leu Arg Leu Leu Leu Leu Pro Val Val Leu Leu
            35                  40                  45

Phe Ile Phe Leu Pro Leu Arg Leu Ser Ser Phe His Leu Gly Gly Pro
50                  55                  60

Thr Ala Leu Tyr Leu Val Trp Leu Ala Asn Phe Lys Leu Leu Leu Phe
65                  70                  75                  80

Ala Phe His Leu Gly Pro Leu Ser Asn Pro Ser Leu Ser Leu Leu His
            85                  90                  95

Phe Ile Ser Thr Thr Leu Leu Pro Ile Lys Phe Arg Asp Asp Pro Ser
            100                 105                 110

Asn Asp His Glu Lys Asn Lys Arg Thr Leu Ser Phe Glu Trp Arg Lys
            115                 120                 125

Val Val Leu Phe Val Ala Lys Leu Val Phe Phe Ala Gly Ile Leu Lys
130                 135                 140

Ile Tyr Glu Phe Arg Lys Asp Leu Pro His Phe Val Ile Ser Val Leu
145                 150                 155                 160

Tyr Cys Phe His Phe Tyr Leu Gly Thr Glu Ile Thr Leu Ala Ala Ser
                165                 170                 175

Ala Val Ile Ala Arg Ala Thr Leu Gly Leu Asp Leu Tyr Pro Gln Phe
            180                 185                 190

Asn Glu Pro Tyr Leu Ala Thr Ser Leu Gln Asp Phe Trp Gly Arg Arg
            195                 200                 205

Trp Asn Leu Met Val Ser Asp Ile Leu Gly Leu Thr Thr Tyr Gln Pro
210                 215                 220

Val Arg Arg Val Leu Ser Arg Trp Val Arg Leu Arg Trp Glu Val Ala
225                 230                 235                 240

Gly Ala Met Leu Val Ala Phe Thr Val Ser Gly Leu Met His Glu Val
                245                 250                 255

Phe Phe Phe Tyr Leu Thr Arg Ala Arg Pro Ser Trp Glu Val Thr Gly
            260                 265                 270

Phe Phe Val Leu His Gly Val Cys Thr Ala Val Glu Met Val Val Lys
            275                 280                 285

Lys Ala Val Ser Gly Lys Val Arg Leu Arg Arg Glu Val Ser Gly Ala
            290                 295                 300

Leu Thr Val Gly Phe Val Met Val Thr Gly Gly Trp Leu Phe Leu Pro
305                 310                 315                 320

Gln Leu Val Arg His Gly Val Asp Leu Lys Thr Ile Asp Glu Tyr Pro
            325                 330                 335

Val Met Phe Asn Tyr Thr Gln Lys Lys Leu Met Gly Leu Leu Gly Trp
            340                 345                 350
```

<210> SEQ ID NO 15
<211> LENGTH: 608
<212> TYPE: PRT
<213> ORGANISM: Arabidopsis thaliana
<220> FEATURE:
<223> OTHER INFORMATION: wax synthase

<400> SEQUENCE: 15

Met Arg Glu Phe Val Gly Asp Gly Gly Gly Pro Pro Arg Trp Phe Ser

-continued

```
1               5                   10                  15
    Pro Leu Glu Cys Gly Ala Gln Ala Thr Asn Ser Pro Leu Leu Leu Tyr
                    20                  25                  30

Leu Pro Gly Ile Asp Gly Thr Gly Leu Gly Leu Ile Arg His His Lys
                    35                  40                  45

Lys Leu Gly Glu Ile Phe Asp Ile Trp Cys Leu His Ile Pro Val Ser
                    50                  55                  60

Asp Arg Thr Pro Val Lys Asp Leu Val Lys Leu Ile Glu Glu Thr Val
    65                  70                  75                  80

Lys Ser Glu Asn Phe Arg Leu Pro Asn Arg Pro Ile Tyr Leu Val Gly
                        85                  90                  95

Glu Ser Ile Gly Ala Cys Leu Ala Leu Asp Val Ala Ala Arg Asn Pro
                    100                 105                 110

Asn Ile Asp Leu Ser Leu Ile Leu Val Asn Pro Ala Thr His Val Asn
                    115                 120                 125

Asn Phe Met Val Gln Pro Leu Ser Gly Met Leu Asn Val Leu Pro Asp
                    130                 135                 140

Gly Leu Pro Thr Leu Leu Glu Asp Ile Phe Asp Phe Gly Phe Lys Gln
    145                 150                 155                 160

Gly Asp Pro Leu Thr Gly Met Leu Asp Ala Leu Ser Asn Glu Phe Ser
                        165                 170                 175

Val Gln Arg Met Gly Gly Val Gly Gly Met Leu Arg Asp Val Leu
                    180                 185                 190

Ala Val Ser Ala Asn Leu Pro Thr Leu Ser Arg Met Phe Pro Lys Asp
                    195                 200                 205

Thr Leu Leu Trp Lys Leu Glu Met Leu Lys Tyr Ala Ile Ala Ser Val
    210                 215                 220

Asn Ser His Ile Tyr Ser Val Arg Ala Glu Thr Leu Ile Leu Leu Ser
    225                 230                 235                 240

Gly Arg Asp His Trp Leu Leu Lys Glu Glu Asp Ile Asp Arg Tyr Ser
                        245                 250                 255

Arg Thr Leu Pro Lys Cys Ile Val Arg Lys Leu Asp Asp Asn Gly Gln
                    260                 265                 270

Phe Pro Leu Leu Glu Asp Gly Val Asp Leu Ala Thr Ile Ile Lys Cys
                    275                 280                 285

Thr Cys Phe Tyr Arg Arg Gly Lys Ser His Asp His Ile Thr Asp Tyr
                    290                 295                 300

Ile Met Pro Thr Thr Phe Glu Leu Lys Gln Gln Val Asp Asp His Arg
    305                 310                 315                 320

Leu Leu Met Asp Gly Thr Ser Pro Val Met Leu Ser Thr Leu Glu Asp
                        325                 330                 335

Gly Thr Val Val Arg Ser Leu Glu Gly Leu Pro Ser Glu Gly Pro Val
                    340                 345                 350

Leu Tyr Val Gly Tyr His Met Ile Leu Gly Phe Glu Leu Ala Pro Met
                    355                 360                 365

Val Ile Gln Leu Met Thr Glu Arg Asn Ile His Leu Arg Gly Leu Ala
                    370                 375                 380

His Pro Met Leu Phe Lys Asn Leu Gln Asp Ser Leu Val Asp Thr Lys
    385                 390                 395                 400

Met Phe Asp Lys Tyr Lys Ile Met Gly Gly Val Pro Val Ser His Phe
                        405                 410                 415

Asn Ile Tyr Lys Leu Leu Arg Glu Lys Ala His Val Leu Leu Tyr Pro
                    420                 425                 430
```

```
Gly Gly Val Arg Glu Ala Leu His Arg Lys Gly Glu Glu Tyr Lys Leu
        435                 440                 445

Phe Trp Pro Glu Arg Ser Glu Phe Val Arg Val Ala Ser Lys Phe Gly
        450                 455                 460

Ala Lys Ile Val Pro Phe Gly Val Val Gly Glu Asp Asp Ile Cys Glu
465                 470                 475                 480

Ile Val Leu Asp Ser Asn Asp Gln Arg Asn Ile Pro Ile Leu Lys Asp
                485                 490                 495

Leu Met Glu Lys Ala Thr Lys Asp Ala Gly Asn Ile Arg Glu Gly Asp
                500                 505                 510

Glu Ser Glu Leu Gly Asn Gln Glu Cys Tyr Phe Pro Gly Leu Val Pro
        515                 520                 525

Lys Ile Pro Gly Arg Phe Tyr Tyr Tyr Phe Gly Lys Pro Ile Glu Thr
        530                 535                 540

Ala Gly Lys Glu Lys Glu Leu Lys Asp Lys Glu Lys Ala Gln Glu Leu
545                 550                 555                 560

Tyr Leu Gln Val Lys Ser Glu Val Glu Gln Cys Ile Asp Tyr Leu Lys
                565                 570                 575

Val Lys Arg Glu Ser Asp Pro Tyr Arg His Leu Leu Pro Arg Met Leu
                580                 585                 590

Tyr Gln Ala Ser His Gly Trp Ser Ser Glu Ile Pro Thr Phe Asp Leu
        595                 600                 605
```

PRODUCTION OF INSECT PHEROMONE PRECURSORS IN PLANTS

SEQUENCE REFERENCE

This application references and incorporates by reference an ASCII file filed by EFS-Web, including amino acid SEQ ID NOS. 1-15. The ASCII file is 51,838 bytes, named "SEQUENCE LISTING v2 ISCA 029US.txt" created on Apr. 4, 2019.

FIELD OF INVENTION

Wax esters (WE) and triacylglycerols (TAG) can be accumulated in large amounts in plant cells. The present invention relates to insect pheromone precursors which are produced as components of WE or TAG in plants. Further the invention concerns means and methods for the production of plant cells producing WE and/or TAG containing insect pheromone precursors in form of either a fatty acid or a fatty alcohol. Finally the invention relates to the extraction of insect pheromone precursors and use of the insect pheromone precursors in the manufacturing of insect pheromones from WE and TAG.

BACKGROUND OF INVENTION

Pheromones are environmentally friendly alternatives to the use of traditional pesticides for control of insect pests and indeed synthetic pheromones are annually produced in huge amounts for this purpose. The use of pheromones for control of pest insects has many advantages over the use of traditional pesticides. The pheromones are non-toxic; they have no adverse effects on non-target organisms, they do not kill parasitoids or other beneficial insects, and the risks of resistance being developed in the pests are small. Even in terms of profit and reduction in damage pheromones often compare favorably to the use of insecticides. In the case of treating cabbage against diamondback moth infestation, pheromone-based integrated pest management was both cheaper ($62 relative to $123 per ha) and the gross profit was higher (ca $800 compared to $456 per ha) than in ordinary practice with insecticides [1]. The global market for pheromone-based control products is currently estimated to approximately $200 million.

Although prices have come down significantly for synthetic made pheromones commonly used, most prices remain high. Labor costs for the application of pheromones may be high and longevity of the formulations is a concern. Standard approaches to pheromone synthesis either require the use of hazardous chemicals or may result in the production of hazardous waste by-products [2, 3]. The inherent waste problem in synthetic pheromone production could be avoided by inventing and developing an innovative green chemistry alternative, i.e, the synthesis of pheromones or pheromone precursors in a cost-effective and environmentally friendly plant factory. Our strategy involves the use of a cost effective plant factory expressing a suite of biosynthetic enzymes for production of moth pheromones.

Female moths emit species-specific pheromone blends that attract males of the same species over long distances [4]. A majority of the identified moth pheromone compounds consist of fatty acid derivatives produced de novo in the pheromone gland [5, 6]. Their biosynthesis typically involves desaturation of fatty acids, reduction to primary alcohols and further modification to produce acetates or aldehydes.

Great advances have been made during the last 15 years with respect to our understanding of the molecular basis of moth pheromone biosynthesis [7, 8]. Heterologous expression systems have allowed the confirmation of the function of many desaturases [9-13] and fatty-acyl reductases (FARs) [14-16]. Desaturases introduce double bonds in different positions in fatty acids with different chain-length. The functionally characterized FARs converts fatty acyl moieties into fatty alcohols.

Transgenic plants have also proven useful to express enzymes from insects. For example, transgenic plants produced a pheromone precursor upon introduction of a moth desaturase [17] and an aphid alarm pheromone has been produced from endogenous plant sesquiterpene by expression of an (E)-β-farnesene synthase cDNA [18]. Transformation of plants is performed by standard practices and regulation of integrated genes can direct their expression to tissues of choice such as seeds or leaf.

SUMMARY OF THE INVENTION

The present invention demonstrates for the first time the feasibility of the production and accumulation of large amounts of insect (moth) pheromone precursors in transgenic plants, such as in the leaf cells and oil seed cells as components of WE and/or TAG by the concerted expression of a suite of biosynthetic enzymes.

In a first aspect the invention relates to an isolated insect pheromone precursor or a mixture of isolated insect pheromone precursors produced in plant cells (in vivo) as part of plant wax esters and/or plant triacylglycerols,
  a. wherein the wax ester in the plant is at least modified by a desaturase, fatty acyl reductase and a wax ester synthase during synthesis of the pheromone precursor and/or
  b. wherein the plant triacylglycerol in the plant is at least modified by a desaturase during synthesis of the pheromone precursor.

In a second aspect the invention relates to a genetically modified plant having incorporated into the genome one or more heterologous gene(s) encoding at least a desaturase, fatty acyl reductase and a wax ester synthase or a desaturase, wherein the plant produces insect pheromone precursors.

In a third aspect the invention relates to an isolated insect pheromone precursor from the transgenic plant disclosed above.

In a final aspect the invention relates to the use of the isolated insect pheromone precursor or the plants according to any of preceding claims for the production of insect pheromones.

The present invention further relates to the extraction of WE and TAG containing insect pheromone precursors from said plant tissues. Methods are described, that are known to persons skilled in the art of organic chemistry, to purify and convert the insect pheromone precursors in WE and TAG into insect pheromone molecules/particles.

By the invention it is for the first time possible to produce insect pheromone precursors environmentally friendly, in large amounts limiting the used chemical reactions to cheap and more benign chemistry.

BRIEF DESCRIPTION OF THE FIGURES

FIG. 1 shows the synthesis of the insect pheromone precursors and the pathway of their incorporation into either wax ester (WE) or triacylglycerol (TAG). An optional step is the enhanced supply of suitable substrates of 12-16 carbon compounds by the release through a plastid localized acyl-ACP thioesterase, exemplified by CpFATB2. Acyl-CoA substrates are then utilized by desaturases introducing desaturation in specific positions on the acyl chain and with steric configurations that are found in insect pheromone components. The desaturated acyl-CoAs are then either utilized for TAG synthesis or in the presence of a wax synthase incorporated into a wax ester. To form a wax ester, an alcohol component is also needed which is provided by a fatty acyl reductase action on the formed desaturated acyl-CoA. In this aspect both the alcohol as well as the fatty acid part of the wax ester can subsequently be utilized for insect pheromone component production.

DETAILED DESCRIPTION OF THE INVENTION

Definitions

In the context of the present application and invention, the following definitions apply:

The term "genetic modification" means the introduction of homologous and/or heterologous foreign nucleic acid molecules into the genome of a plant cell or into the genome of a plant, wherein said introduction of these molecules leads to an accumulation of insect pheromone precursors as constituents of WE and/or TAG in seed or vegetative tissue of a plant.

The term "heterologous" as used herein describes a relationship between two or more elements which indicates that the elements are not normally found in proximity to one another in nature. Thus, for example, a polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). An example of a heterologous polypeptide is a polypeptide expressed from a recombinant polynucleotide in a transgenic organism. Heterologous polynucleotides and polypeptides are forms of recombinant molecules.

Genes and Enzymes for the Production of Insect Pheromone Precursors and Introduction into WE and TAG in Plant Cells.

In one embodiment the invention relates to an isolated insect pheromone precursor or a mixture of isolated insect pheromone precursors produced in plant cells (in vivo) as part of plant wax esters and/or plant triacylglycerols, a. wherein the wax ester in the plant is at least modified by a desaturase, fatty acyl reductase and a wax ester synthase during synthesis of the pheromone precursor and/or
b. wherein the plant triacylglycerol in the plant is at least modified by a desaturase during synthesis of the pheromone precursor.

The produced plant wax esters and/or plant triacylglycerols may then be used for the production of insect pheromones and further used for pest management. By the invention the plant wax esters and/or plant triacylglycerols can be produced by an environmental friendly process as well as in an economically beneficial way. The amount of isolated insect pheromone precursor or a mixture of isolated insect pheromone precursors may further be enhanced by a plastidic acyl-ACP thioesterase providing an increased amount of suitable substrates in the plant either prior or after other modifications. However, the modifications occur in vivo in the plant by enzymes expressed by the plant prior to that the insect pheromone precursors are to be isolated. The genes that are to produce the insect pheromone precursors are heterologous genes and express at least the following enzymes acyl-CoA desaturase, fatty acyl reductase, wax ester synthase and/or plastidic acyl-ACP thioesterase, which are involved in the provision of substrates or synthesis of the wax esters and/or triacylglycerols. Examples includes precursors selected from the group consisting of unsaturated fatty acids (E)-11-tetradecanoyl (E11-14), (Z)-11-tetradecanoyl (Z11-14) and (Z)-11-hexadecanoyl (Z11-16) and unsaturated alcohols (E)-11-tetradecenol (E11-14:OH), (Z)-11-tetradecenol (Z11-14:OH) and (Z)-11-hexadecenol (Z11-16:OH) or a mixture thereof. The isolated insect pheromone precursor or a mixture thereof, may be produced in the seeds or vegetative tissue of the plant.

In one embodiment, the invention relates to a genetically modified plant having incorporated into the genome a heterologous gene encoding at least an acyl-CoA desaturase, fatty acyl reductase and a wax ester synthase or an acyl-CoA desaturase, wherein the plant produced insect pheromone precursors incorporated as part of wax ester and/or TAG. The genetically modified plant may further have incorporated in the genome a heterologous gene encoding at least a plastidic acyl-ACP thioesterase, such as having at least a desaturase, fatty acyl reductase, a plastidic acyl-ACP thioesterase and a wax ester synthase or a desaturase and a plastidic acyl-ACP thioesterase.

In one example the acyl-CoA pool for moth pheromone precursors is optimized in the plant cells by the introduction of genes encoding plastidic acyl-ACP thioesterases that release acyl chains of a desired length for moth pheromone precursor production. Moth pheromone precursors are first produced as monounsaturated acyl-CoA and monounsaturated fatty alcohol. Insect genes encoding desaturases are used to firstly produce desired acyl-CoA dependent on the specific desaturase and insect genes encoding fatty acyl reductases (FAR) are used to secondly reduce monounsaturated acyl-CoA into their corresponding alcohols.

Insect pheromone precursors produced by desaturases and in the case of wax esters, also by FAR, are then used as substrates for the assembly of TAG and WE. To introduce insect pheromone precursors into WE, genes encoding the function of wax ester synthase are used. Examples of genes utilized encoding a function of wax ester synthase are, but not limited to, *Arabidopsis thaliana* phytol ester synthase 1 (AtPES1), *Arabidopsis thaliana* phytol ester synthase 2 (AtPES2) or *Euglena gracilis* wax ester synthase (EgWS) [19, 20]. As native enzymes, AtPES1 and AtPES2 are imported into plastid organelles. For use in the present invention DNA sequences coding for a signal transit peptide may be deleted from AtPES1 and AtPES2 and replaced with an ATG codon for new translation start. Enzymes are preferentially targeted to the endoplasmic reticulum (ER). Means for attaching ER localization or retainment signals are well known in the art. Monounsaturated acyl-CoA insect precursors as well as monounsaturated fatty alcohol insect pheromone precursors are introduced into the WE. For TAG produced monounsaturated acyl-CoA insect pheromone precursors can be accepted by available enzymes in the plant system for TAG assembly, although the introduction of genes encoding enzymes preferentially utilizing the medium chain monounsaturated acyl-CoA insect pheromone precursors may be preferred. Examples of genes used to enhance the introduction of monounsaturated acyl-CoA insect pheromone precursors into TAG are, but not limited to, glycerol-3-phosphate acyl transferase, lysophosphatidic acid acyltransferase and diacylglycerols acyltransferase encoding genes. In order to enhance the production of TAG and WE, transcription factors enhancing plant cell fatty acid synthesis such as, but not limited to, WRINKLED1 type of transcription factors [21] can be co-expressed. To prevent degradation of WE and TAG produced in leaf cells, oleosin genes can be co-expressed.

The genetically modified plant disclosed above may comprise at least one gene that encodes a polypeptide, wherein the polypeptide is/are selected from the group consisting of SEQ ID NO: 1, 2, 3, 4, 5, 6, 7, 8, 9, 10, 11, 12, 13, 14 or 15 or a polypeptide having 60% identity to a polypeptide with an amino acid sequence of SEQ ID NO: 1, 2, 3, 4, 5, 6, 7, 8, 9, 10, 11, 12, 13, 14 or 15. The term "identity" means a sequence identity over the whole length of the coding region of at least 60%, such as 65, 70, 75, 80, 85, 90, 91, 92, 93, 94, 95, 96, 97, 98 or 99%.

The term "identity" is to be understood to mean the number of amino acids/nucleotides (identity) corresponding with other proteins/nucleic acids, expressed as a percentage. Identity is preferably determined by comparing SEQ ID NO: 1, 2, 3, 4, 5, 6, 7, 8, 9, 10, 11, 12, 13, 14 or 15 for amino acids with other proteins acids with the help of computer programs. If sequences that are compared with one another have different lengths, the identity is to be determined in such a way that the number of amino acids, which have the shorter sequence in common with the longer sequence, determines the percentage quotient of the identity. Preferably, identity is determined by means of the computer program ClustalW, which is well known and available to the public (Thompson et al., Nucleic Acids Research 22 (1994), 4673-4680). ClustalW is made publicly available by Julie Thompson (Thompson@EMBL-Heidelberg.DE) and Toby Gibson (Gibson@EMBL-Heidelberg.DE), European Molecular Biology Laboratory, Meyerhofstrasse 1, D 69117 Heidelberg, Germany. ClustalW can also be downloaded from different Internet sites, including the IGBMC (Institut de Genetique et de Biologie Moleculaire et Cellulaire, B.P.163, 67404 Illkirch Cedex, France; ftp://ftp-igbmc.u-strasbg.fr/pub/) and the EBI (ftp://ftp.ebi.ac.uk/pub/software/) as well as from all mirrored Internet sites of the EBI (European Bioinformatics Institute, Wellcome Trust Genome Campus, Hinxton, Cambridge CB10 1SD, UK).

In one embodiment the genetically modified plant comprises at least one, two, three or four genes that encodes a polypeptide, wherein the polypeptide is/are selected from the group consisting of SEQ ID NO: 1, 2, 3, 4, 5, 6, 7, 8, 9, 10, 11, 12, 13, 14 or 15 or a polypeptide having 60% identity to a polypeptide with an amino acid sequence of SEQ ID NO: 1, 2, 3, 4, 5, 6, 7, 8, 9, 10, 11, 12, 13, 14 or 15. One example being a genetically modified plant which comprises one, two, three or four polypeptides selected from the group consisting of SEQ ID NO: 1 and 2, 3, 4, 5 or 6 and 7, 8, 9 or 10 and 11, 12, 13, 14 or 15.

The genetically modified plant may be any plant species capable of accumulating oil in the form of WE and/or TAG in vegetative or seed tissue. For seed tissue, in particular oil seed crops as *Camelina sativa, Crambe abyssinica Brassica* species are applicable while for vegetative tissue species capable of producing large amounts of biomass such as tobacco, *miscanthus* or sugar beet. However, depending on where the plants are to be produced other tissues may be the choice as well as other species.

The genetically modified plant described above may express/produce the wax esters and/or triacylglycerol in the seeds or in the vegetative tissue or in any other useful tissue. In one example the wax esters and/or triacylglycerol are produced in the seeds.

In another embodiment the invention relates to isolated insect pheromone precursor, wherein the isolated insect pheromone precursors are isolated from a transgenic plant, such as the transgenic plant (genetically modified plant) described above.

Expression Vectors for the Introduction of Genes into a Heterologous Production System By expression vector is meant a vector suitable for the stable introduction of genes into an organism of choice and their subsequent controlled expression in a desirable context. For expression of a gene encoding an enzymatic function a promoter is commonly attached to the front end of the gene while a terminator is attached to the back end of the gene. The promoter defines in which tissue, under which conditions and to which extend a gene is expressed. The terminator defines the end of a gene and terminating transcription. Promoters and terminators are well known in the art. Examples of promoters are for seed expression the napin or glycinin promoter and for vegetative tissue the CaMV35S promoter but other promoters known in the art can be used to practice the invention.

Other examples of promoters are, for example, he ubiquitin promoter from maize for constitutive expression, the patatin promoter B33 for tuber-specific expression in potatoes, the USP promoter, the phaseolin promoter, promoters of zein genes from maize, glutelin promoter or shrunken-1 promoter.

Furthermore, a termination sequence (polyadenylation signal) may be present, which is used for adding a poly-A tail to the transcript. A function in the stabilisation of the transcripts is ascribed to the poly-A tail. Elements of this type are described in the literature and can be exchanged at will.

An expression vector may contain one or several of the genes which are to be introduced. Genes on an expression vector to be introduced for the production of insect pheromone precursors as part of WE and TAG may be expressed from the same or by different promoters.

Methods for the creation of expression vectors according to the invention are known to the person skilled in the art, and include genetic methods such as bonding nucleic acid molecules by way of ligation, genetic recombination, or new synthesis of nucleic acid molecules, for example (see e.g. Sambrok et al., Molecular Cloning, A Laboratory Manual, 3rd edition (2001) Cold Spring Harbour Laboratory Press, Cold Spring Harbour, N.Y. ISBN: 0879695773, Ausubel et al., Short Protocols in Molecular Biology, John Wiley & Sons; 5th edition (2002), ISBN: 0471250929).

Transformation and Regeneration

By transformation is meant the stable introduction of expression vectors enabling the production of insect pheromone precursors and their introduction into WE and TAG. The transformation of plants is standard technology and well known in the art. Commonly this is performed by *Agrobacterium tumefaciens* transformation of plant tissues. Well known in the art is that different tissues of different species are differently accessible for transformation. Plant transformation is as well known in the art not limited to *Agrobacterium tumefaciens* but genes can also be introduced by other means well-known for a person skilled in the art. To select for which cells have stably introduced desired genes, commonly a selective marker is contained on the expression vector used for transformation. Examples of selection agents among others are kanamycin, hygromycin and BASTA but as well known in the art different selection systems can be used for successful selection of cells which have stably integrated genes for expression. Methods for the regeneration of shoots from selected transgenic cells are well known in the art. Regenerated plants can be analyzed for their transgenic status by PCR or Southern blotting and the expression of genes can be analyzed by PCR or Northern blotting. Translation into corresponding proteins can be analyzed by Western.

Cultivation of Plant Material for Extraction of WE and TAG Containing Insect Pheromone Precursors The transgenic plants can be grown either in climate chambers, in greenhouse or in field. Harvesting of leaf or seed material for WE and TAG containing insect pheromone precursors is done at the optimal stage of accumulation per area cultivated. For production of pheromone precursors in leaves, any transformable broad leaf plant is preferentially used. For production of pheromone precursors in seeds any transformable oil seed producing plant can be used. *Nicotiana tabaccum* could be used for transformation of genes for insect precursor production as components of WE and/or TAG in vegetative tissue while *Camelina sativa* is an example of a plant species for transformation of genes for insect precursor production as components of WE and/or TAG in oil seeds.

Producing Insect Pheromones from Harvested Material

All chemical steps described below are familiar to persons skilled in the art of organic chemistry.

1) Extraction of leaves or seed, depending on the tissue specificities of the promoters used to govern the expression of the introduced genes. The extraction of the tissue with organic solvents such as n-heptane and n-hexane will yield fractions with TAG and WE in high purity.

2) The production of active pheromone from oil with wax esters containing precursor pheromone fatty alcohol can be done by fractionation and chemical conversion procedures known to the person skilled in the art by following methods, but not excluding other known methods. The wax esters can be separated from triacylglycerol molecules by e.g. short path distillation, by crystallization, by silica gel column chromatography or by mild saponification of the triacylglycerols in the oil by sodium or potassium hydroxide in water solution at room temperature and extracting the intact wax esters with organic solvent, i.e. hexane. The wax esters are hydrolyzed to fatty acid and fatty alcohols by treatment with sodium or potassium hydroxide in water solution at elevated temperature. The fatty alcohols are extracted into organic solvent such as heptane and acetylated with treatment with acetylchloride or acetic acid anhydride to yield the final active pheromone. In case of aldehyde pheromone molecules, the alcohol can be partially re-oxidized to yield a fatty aldehyde. Acetylated fatty alcohols and fatty aldehydes can easily be separated from the fatty acids by e.g. distillation. The TAG fraction can easily be hydrolyzed by alkali to yield free fatty acids. The pheromone precursor component fatty acid can be separated from other fatty acids by different means such as distillation or by reverse phase chromatography. The carboxylic group of the fatty acid can then be selectively reduced without reducing the double bonds to yield the alcohol component of the pheromone. The fatty alcohol can either be acetylated in case of acetylated pheromones as described above or partially oxidized to aldehyde to yield an aldehyde pheromone.

In a final embodiment the invention relates to the use of the isolated insect pheromone precursor or the plants according to any of preceding claims for the production of pheromones.

EXAMPLES

Example 1

Production of Insect Pheromone Precursors as Constituents of Wax Esters (WE)

For precursor production as constituents of wax ester in seed oil, genes coding for *Cuphea palustris* plastidic acyl-ACP thioesterase (CpFATB2), *Argyrotaenia velutinana* desaturase (AveΔ11), *Amyelois transitella* desaturase (AtrΔ11), *Helicoverpa armigera* fatty acyl reductase (HarFAR) and the mature form of *Arabidopsis thaliana* phytol ester synthase 2 lacking plastid transit peptide sequence (mAtPES2) were respectively cloned between a glycinin or napin promoter and a glycinin or nopaline synthase terminator. The genes fused to glycinin or napin promoter and glycinin or nopaline synthase terminator were inserted between T-DNA right and left border sequences of a binary vector where also an nptII gene for selection of transgenic cells was situated. Camelina *sativa* plants were transformed using floral dipping and produced seeds germinated on kanamycin containing medium. Transformed plants were selfed and seeds collected upon maturation. Lipids were extracted from seeds and then separated using thin layer chromatography (TLC). The WE fraction was identified using a WE standard and samples were scraped from the TLC plate. The wax ester samples were hydrolyzed and methyl esters (ME) and fatty alcohols were separated and identified using GC/MS yielding (E)-11-tetradecanoyl-ME (E11-14-ME), (Z)-11-tetradecanoyl-ME (Z11-14-ME), (Z)-11-hexadecanoyl-ME (Z11-16-ME) and corresponding alcohols (E)-11-tetradecenol (E11-14:OH), (Z)-11-tetradecenol (Z11-14:OH), (Z)-11-hexadecenol (Z11-16:OH).

For precursor production as constituents of wax ester in vegetative leaf tissue, genes coding for *Cuphea palustris* plastidic acyl-ACP thioesterase (CpFATB2), *Argyrotaenia velutinana* desaturase (AveΔ11), *Amyelois transitella* desaturase (AtrΔ11), *Helicoverpa armigera* fatty acyl reductase (HarFAR), *Arabidosis thaliana* WRINKLED 1 (AtWRI1) and the mature form of *Arabidopsis thaliana* phytol ester synthase 2 lacking plastid transit peptide sequence (mAtPES2) were respectively cloned between a CaMV35S promoter and a nopaline synthase terminator. The genes fused to CaMV35S promoter and nopaline synthase terminator were inserted between T-DNA right and left border sequences of a binary vector where also an nptII gene for selection of transgenic cells was situated. *Nicotiana* tabaccum leaf discs were transformed and shoots regenerated on kanamycin containing medium. Shoots were transferred to soil and allowed to develop. Lipids were extracted from expanded leaves and then separated using thin layer chromatography (TLC). The WE fraction was identified using a WE standard and samples were scraped from the TLC plate. The wax ester samples were hydrolyzed and methyl esters (ME) and fatty alcohols were separated and identified using GC/MS yielding (E)-11-tetradecanoyl-ME (E11-14-ME), (Z)-11-tetradecanoyl-ME (Z11-14-ME), (Z)-11-hexadecanoyl-ME (Z11-16-ME) and corresponding alcohols (E)-11-tetradecenol (E11-14:OH), (Z)-11-tetradecenol (Z11-14:OH), (Z)-11-hexadecenol (Z11-16:OH). Tobacco leaves infiltrated with *Agrobacterium* containing different gene constructs in the following two combinations, Cpa- FATB2+HarFAR+AveΔ11+mAtPES2+AtWRI1, CpaFATB2+HarFAR+AtrΔ11+mAtPES2+AtWRI1 Yielded 0.75 and 0.91 µg 14:1 and 0 and 2.83 µg 16:1 leaf fresh weight respectively as insect pheromone precursor constituents of isolated wax ester.

Example 2

Production of Desaturated Insect Pheromone Precursors as Constituent of Triacylglycerols (TAG).

For precursor production as constituents of triacylglycerol (TAG) in seed oil, genes coding for *Cuphea palustris* plastidic acyl-ACP thioesterase (CpFATB2), *Choristoneura parallela* desaturase (CpaE11), *Argyrotaenia velutinana* desaturase (AveΔ11), *Amyelois transitella* desaturase (AtrΔ11) were respectively cloned between a glycinin or napin promoter and a glycinin or nopaline synthase terminator. The genes fused to glycinin or napin promoter and glycinin or nopaline synthase terminator were inserted between T-DNA right and left border sequences of a binary vector where also an nptII gene for selection of transgenic cells was situated. Camelina *sativa* plants were transformed using floral dipping and produced seeds germinated on kanamycin containing medium. Transformed plants were selfed and seeds collected upon maturation. Lipids were extracted from seeds and then separated using thin layer chromatography (TLC). The TAG fraction was identified using a TAG standard and samples were scraped from the TLC plate. The TAG samples were hydrolyzed and methyl esters (ME) were separated and identified using GC/MS yielding (E)-11-tetradecanoyl-ME (E11-14-ME), (Z)-11-tetradecanoyl-ME (Z11-14-ME), (Z)-11-hexadecanoyl-ME (Z11-16-ME).

*Camelina sativa* (high myristic) transformed with CpaE11 yielded isolated seed TAG containing in individual seeds 7.1, 7.2, 7.6, 7.6, 8.0, 8.2 and 9.2% E11-14 of total fatty acids. *Camelina sativa* (high myristic) transformed with AveΔ11 yielded isolated seed TAG containing in individual seeds 2.0, 2.1, 2.2 and 2.3% E11-14 and 6.0, 6.1, 6.5 and 6.8% Z11-14 of total fatty acids. *Camelina sativa* (high palmitic) transformed with AtrΔ11 yielded isolated seed TAG containing in individual seeds 17.3, 17.4, 17.7, 19.2 and 28.2% Z11-16 of total fatty acids. For precursor production as constituents of TAG in vegetative leaf tissue, genes coding for *Cuphea palustris* plastidic acyl-ACP thioesterase (CpFATB2), *Argyrotaenia velutinana* desaturase (AveΔ11), *Amyelois transitella* desaturase (AtrΔ11) and *Arabidosis thaliana* WRINKLED 1 (AtWRI1) were respectively cloned between a CaMV35S promoter and a nopaline synthase terminator. The genes fused to CaMV35S promoter and nopaline synthase terminator were inserted between T-DNA right and left border sequences of a binary vector where also an nptII gene for selection of transgenic cells was situated. *Nicotiana tabaccum* leaf discs were transformed and shoots regenerated on kanamycin containing medium. Shoots were transferred to soil and allowed to develop. Lipids were extracted from expanded leaves and then separated using thin layer chromatography (TLC). The TAG fraction was identified using a TAG standard and samples were scraped from the TLC plate. The TAG samples were hydrolyzed and methyl esters (ME) were separated and identified using GC/MS yielding (E)-11-tetradecanoyl-ME (E11-14-ME), (Z)-11-tetradecanoyl-ME (Z11-14-ME), (Z)-11-hexadecanoyl-ME (Z11-16-ME).

Example 3

The production of active pheromone from TAG (triacylglycerols) containing precursor pheromone fatty acids was performed by fractionation and chemical conversion procedures. The oil was treated with water free methanol containing acid or alkali as catalysts to yield fatty acid methyl esters. The fatty acid of interest was purified as methyl esters by short path distillation or by crystallization and the fatty acid was converted to corresponding fatty acid alcohol by reaction with lithiumaluminium hydride or tri-tert-butoxyaluminumlithium hydride or by selective catalytic hydrogenation by high pressure hydrogenation. Resulting fatty alcohol was acetylated by treatment with acetylchloride or acetic acid anhydride to yield the final active pheromone molecule.

Example 4

The production of active pheromone from oil with wax esters containing precursor pheromone fatty alcohol was performed by fractionation and chemical conversion procedures. The wax esters were separated from triacylglycerol molecules by short path distillation, by crystallization, by silica gel column chromatography or by mild saponification of the triacylglycerols in the oil by sodium or potassium hydroxide in water solution at room temperature and extracting the intact wax esters with hexane. The wax esters were hydrolyzed to fatty acid and fatty alcohols by treatment with sodium or potassium hydroxide in water solution at elevated temperature. The fatty alcohols were extracted into heptane and acetylated with treatment with acetylchloride or acetic acid anhydride to yield the final active pheromone.

REFERENCES

1. Reddy, G. V. P. and A. Guerrero, *Pheromone-based integrated pest management to control the diamondback moth Plutella xylostella in cabbage fields*. Pest Management Science, 2000. 56(10): p. 882-888.
2. Mori, K., *The Synthesis of Insect Pheromones, 1979-1989*, in *Total Synthesis of Natural Products*2007, John Wiley & Sons, Inc. p. 1-521.
3. Mori, K., *Chemical Synthesis of Hormones, Pheromones and Other Bioregulators*2010: John Wiley & Sons Ltd.
4. Wyatt, T. D., *Pheromones and animal behaviour: communication by smell and taste*. Pheromones and animal behaviour: communication by smell and taste.2003. i-xv, 1-391.
5. Ando, T., S. Inomata, and M. Yamamoto, *Lepidopteran sex pheromones*. Chemistry of Pheromones and Other Semiochemicals I, 2004. 239: p. 51-96.
6. Tillman, J. A., et al., *Insect pheromones—an overview of biosynthesis and endocrine regulation*. Insect Biochemistry and Molecular Biology, 1999. 29(6): p. 481-514.
7. Knipple, D. C. and W. L. Roelofs, *Molecular biological investigations of pheromone desaturases*. Insect pheromone biochemistry and molecular biology: the biosynthesis and detection of pheromone and plant volatiles., ed. G. J. Blomquist and R. G. Vogt2003. 81-106.
8. Lassance, J.-M., et al., *Functional consequences of sequence variation in the pheromone biosynthetic gene pgFAR for Ostrinia moths*. Proceedings of the National Academy of Sciences of the United States of America, 2013. 110(10): p. 3967-3972.
9. Hao, G., et al., *Characterization of Z/E11-and Z9-desaturases from the obliquebanded leafroller moth, Choristoneura rosaceana*. Journal of insect science (Online), 2002. 2: p. 26-26.

10. Lienard, M. A., et al., *Key biosynthetic gene subfamily recruited for pheromone production prior to the extensive radiation of Lepidoptera.* Bmc Evolutionary Biology, 2008. 8.
11. Liu, W. T., et al., *Moth desaturase characterized that produces both Z and E isomers of Delta 11-tetradecenoic acids.* Insect Biochemistry and Molecular Biology, 2002. 32(11): p. 1489-1495.
12. Liu, W. T., et al., *Desaturases from the spotted fireworm moth (Choristoneura parallela) shed light on the evolutionary origins of novel moth sex pheromone desaturases.* Gene, 2004. 342(2): p. 303-311.
13. Roelofs, W. L., et al., *Evolution of moth sex pheromones via ancestral genes.* Proceedings of the National Academy of Sciences of the United States of America, 2002. 99(21): p. 13621-13626.
14. Lassance, J.-M., et al., *Allelic variation in a fatty-acyl reductase gene causes divergence in moth sex pheromones.* Nature, 2010. 466(7305): p. 486-U7.
15. Lienard, M. A., et al., *Evolution of multicomponent pheromone signals in small ermine moths involves a single fatty-acyl reductase gene.* Proceedings of the National Academy of Sciences of the United States of America, 2010. 107(24): p. 10955-10960.
16. Moto, K. i., et al., *Pheromone gland-specific fatty-acyl reductase of the silkmoth, Bombyx mori.* Proceedings of the National Academy of Sciences, 2003. 100(16): p. 9156-9161.
17. Nesnerova, P., et al., *First semi-synthetic preparation of sex pheromones.* Green Chemistry, 2004. 6(7): p. 305-307.
18. Beale, M. H., et al., *Aphid alarm pheromone produced by transgenic plants affects aphid and parasitoid behavior.* Proceedings of the National Academy of Sciences of the United States of America, 2006. 103(27): p. 10509-10513.
19. Lippold, F., et al., *Fatty Acid Phytyl Ester Synthesis in Chloroplasts of Arabidopsis.* Plant Cell, 2012. 24(5): p. 2001-2014.
20. Teerawanichpan, P. and X. Qiu, *Fatty Acyl-CoA Reductase and Wax Synthase from Euglena gracilis in the Biosynthesis of Medium-Chain Wax Esters.* Lipids, 2010. 45(3): p. 263-273.
21. Cernac, A. and C. Benning, *WRINKLED1 encodes an AP2/EREB domain protein involved in the control of storage compound biosynthesis in Arabidopsis.* Plant Journal, 2004. 40(4): p. 575-585.

The invention claimed is:

1. An insect pheromone precursor or a mixture of insect pheromone precursors produced in plant cells in vivo as part of a plant wax ester or a plant triacylglycerol,
   wherein the insect pheromone precursor or mixture of insect pheromone precursors form a part of the plant wax ester or plant triacylglycerol;
   wherein the plant wax ester in the plant is at least modified by a desaturase, fatty acyl reductase and a wax ester synthase;
   wherein the plant triacylglycerol in the plant is at least modified by a desaturase; and
   wherein the insect pheromone precursor or mixture of insect pheromone precursors are produced in the seeds of the plant.

2. The insect pheromone precursor or a mixture of insect pheromone precursors according to claim 1, wherein the plant wax ester or plant triacylglycerol is modified by a plastidic acyl-ACP thioesterase.

3. The insect pheromone precursor or a mixture of insect pheromone precursors according to claim 1, wherein the desaturase, fatty acyl reductase, or wax ester synthase are encoded by heterologous genes.

4. The insect pheromone precursor or a mixture of insect pheromone precursors according to claim 1, wherein the insect pheromone precursor or mixture of insect pheromone precursors are selected from the group consisting of unsaturated fatty acids (E)-11-tetradecanoyl (E 11-14), (Z)-11-tetradecanoyl (Z11-14:OH) and (Z)-11-hexadecanoyl (Z11-16) and unsaturated alcohols (E)-11-tetradecenol (E11-14:OH), (Z)-11-tetradecenol (Z11-14:OH) and (Z)-11-hexadecenol (Z11-16:OH) or a mixture thereof.

5. The insect pheromone precursor or a mixture of insect pheromone precursors according to claim 2, wherein the plastidic acyl-ACP thioesterase is encoded by a heterologous gene.

* * * * *